United States Patent [19]
Wert et al.

[11] Patent Number: 5,969,226
[45] Date of Patent: Oct. 19, 1999

[54] FRETTING WEAR MACHINE

[75] Inventors: James J. Wert; Miangui Xue; Pedro C. Bastias, all of Nashville, Tenn.

[73] Assignee: The United States of America as represented by the Secretary of the Air Force, Washington, D.C.

[21] Appl. No.: 08/963,157

[22] Filed: Nov. 3, 1997

Related U.S. Application Data

[60] Provisional application No. 60/032,049, Nov. 12, 1996.

[51] Int. Cl.$^6$ .............................. G01N 3/56; G01M 7/02
[52] U.S. Cl. ................................................. 73/7; 73/577
[58] Field of Search ........................... 73/7, 9, 841, 842, 73/577

[56] References Cited

U.S. PATENT DOCUMENTS 3,945,241  3/1976  Brown ............................................ 73/7
4,507,953  4/1985  Vandermeerssche ........................ 73/7
5,377,525  1/1995  Hutchinson et al. ........................ 73/9

*Primary Examiner*—Hezron E Williams
*Assistant Examiner*—Chad Soliz
*Attorney, Agent, or Firm*—Robert L. Nathans

[57] ABSTRACT

A hardened steel ball presses against a vibrating sample to be subject to fretting. The amplitude and frequency of vibration can be precisely controlled by a stack of piezoelectric transducers. The biasing force of the steel ball against the sample can also be precisely controlled by a pulley supported weight that pulls against a movable mass coupled to the steel ball. The movable mass has sufficient inertial mass to eliminate the movement of the ball which might otherwise be produced in reaction to the vibration of the sample, which need not be absolutely flat.

8 Claims, 1 Drawing Sheet

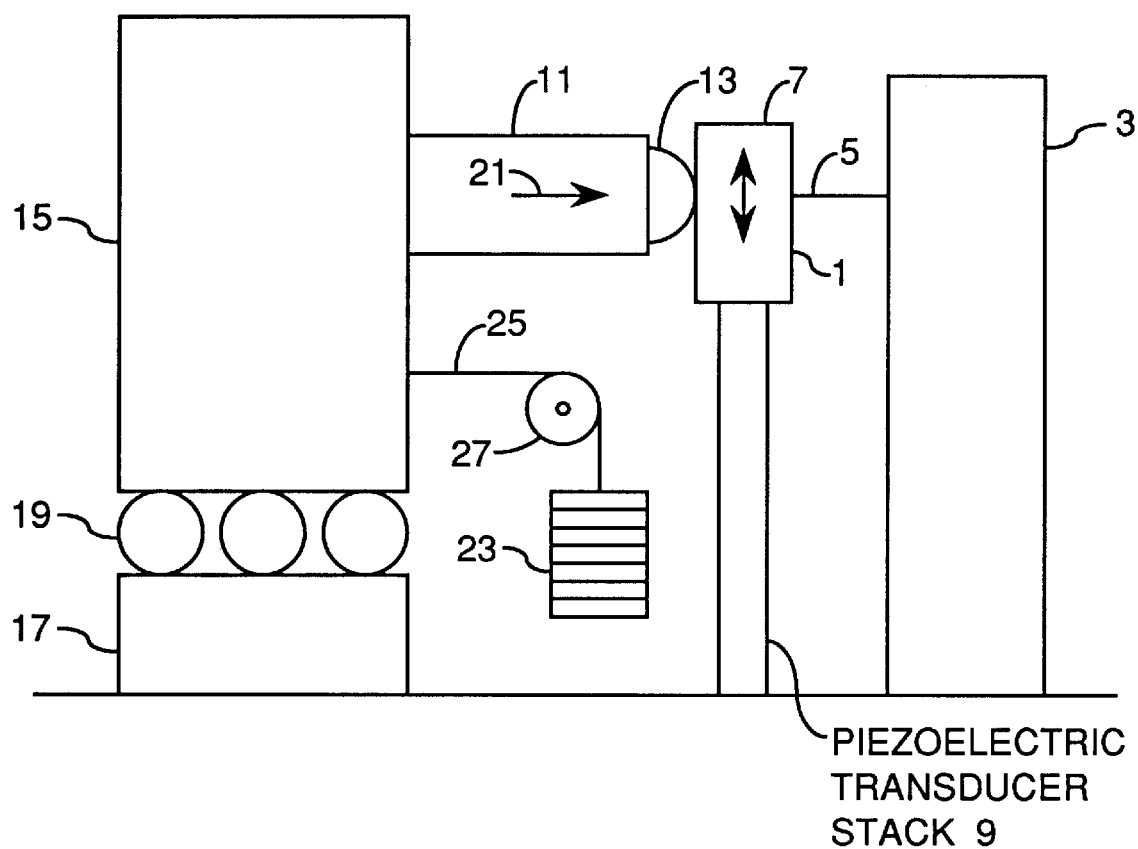

FRETTING WEAR MACHINE

This application claims the benefit of U.S. Provisional Application No. 60/032,049, filed Nov. 12, 1996.

STATEMENT OF GOVERNMENT INTEREST

The invention described herein may be manufactured and used by or for the Government for governmental purposes without the payment of any royalty thereon.

BACKGROUND OF THE INVENTION

The present invention relates to the field of fretting machines. The present inventors presented a paper at The Symposium on Structural Integrity of Aging Aircraft, ASME WAM, San Francisco, on Nov. 12, 1995, entitled "Contribution of Fretting to the Fatigue and Corrosive Deterioration of a Riveted Lap Joint." As stated in the paper, the contacting parts of cyclically loaded, riveted connections present at the skin surface of an aircraft for example, are subject to fretting: small, repeated relative rubbing motions. This fretting produces wear, and can promote fatigue and corrosive damage which foreshortens riveted joint life, to in turn increase the risk of a detrimental aircraft malfunction.

In the experiments extensively described in the aforesaid paper, incorporated by reference herein, fretting of a sample riveted aluminum lap joint was produced by a novel fretting machine, also described in the paper, which is the subject of the present invention. This machine can move the sample through very small, controllable amplitudes and can accurately control rubbing forces applied to the sample.

BRIEF SUMMARY OF ONE EMBODIMENT OF THE INVENTION

A load bearing counter-force member, extending from a movably supported mass, is mechanically biased against a vibrating sample in a direction substantially perpendicular to the vibratory motion of the sample induced by a stack of piezoelectric transducers. A vertically oriented weight, supported by a pulley, creates a precise pulling force upon the movably supported mass, in turn supporting the counter-force member, its mass being sufficient to eliminate lateral reaction movement of the counter-force member which might otherwise be produced in reaction to motion of the sample toward and away from the counter-force member.

BRIEF DESCRIPTION OF THE DRAWING

Various features of the invention will become more apparent upon reading the following description, taken in conjunction with the sole FIGURE, illustrating a preferred embodiment of the invention.

DETAILED DESCRIPTION OF A PREFERRED EMBODIMENT OF THE INVENTION

Referring to the sole FIGURE, sample 1 to be subjected to fretting, is coupled to machine frame portion 3 via a sample support member such as sheet spring 5. A stack of piezoelectric actuator transducers 9 are mechanically coupled to the underside of sample 1 to produce vibration of the sample in the direction indicated by double-headed arrow 7. Load bearing counter-force member 11 is coupled to mass member 15 which is movably supported by bearing 19 upon machine portion 17. The hardened steel ball portion 13 of counter-force member 11 is mechanically biased against sample 1 as indicated by arrow 21. The mechanical biasing means preferably comprises weight 23 coupled to mass 15 via cable 25 which is supported by pulley 27. This constitutes a simple rugged mechanical biasing apparatus for accurately controlling the pulling force produced by weight 23 to the right and thus asserted by the load bearing counter-force member 11 to the right against sample 7 which could comprise the aforesaid riveted aluminum lap joint vibrated in a plane perpendicular to the counter-force asserted by member 11. The machine induces the desired fretting forces applied to the sample, without permitting lateral displacement of the hardened ball 13 of member 11 to the left and away from the sample. This is because movable member 15 has a mass sufficient to eliminate such lateral displacement which could otherwise be produced by the possible skewing or surface irregularity of the lap joint sample 7 as it moves up and down. At the same time, the mass permits transfer of the force of gravity upon weight 23 to the steel ball member 13 via the rollably supported mass member 15 to produce the desired mechanical biasing effect. Fretting is in turn produced by the back and forth vibratory motion of the sample joint pressed against steel ball member 13. The degree of vibrational motion may be readily controlled by the magnitude of the voltages applied to the piezoelectric transducers as is well understood by those skilled in the art. For example, the amplitude of the vibrations in a first direction can be varied typically from between 10 microns and 200 microns, and the vibration frequency may be varied from 0.1 Hz–35 Hz. The rubbing forces applied to the sample in a second direction substantially perpendicular to the first direction may be readily controlled by the magnitude of the weight 23 which weight can be easily changed.

While the preferred machine is as described, variations will occur to the skilled worker in the art, and thus the scope of the invention is to be limited solely by the terms of the following claims and art recognized equivalents thereof. For example, a hardened cylindrical roller can be employed in place of the steel ball 13.

What is claimed is:

1. A fretting wear machine comprising:

(a) sample support means for supporting a sample member for motion in a first direction;

(b) a load bearing counter-force member, coupled to a movable mass, for pressing against said sample member in a second direction perpendicular with respect to said first direction;

(c) biasing means for mechanically biasing said counter-force member against said sample member by asserting a force against said movable mass;

(d) motion inducing means for moving said sample in a plane perpendicular to said second direction; and (e) wherein said movable mass has a mass sufficient to eliminate movement of the counter-force member in response to motion of the sample member.

2. The machine of claim 1 wherein said motion inducing means includes a stack of piezoelectric transducers for vibrating said sample back and forth.

3. The machine of claim 1 wherein said mechanical biasing means includes a pulley for supporting a vertically oriented weight coupled to said movable mass via a cable contacting said pulley.

4. The machine of claim 2 wherein said mechanical biasing means includes a pulley for supporting a vertically oriented weight coupled to said movable mass via a cable contacting said pulley.

5. The machine of claim 1 wherein said load bearing counter-force member includes a hardened ball member for contacting said sample member.

6. The machine of claim 2 wherein said load bearing counter-force member includes a hardened ball member for contacting said sample member.

7. The machine of claim 3 wherein said load bearing counter-force member includes a hardened ball member for contacting said sample member.

8. The machine of claim 4 said load bearing counter-force member includes a hardened ball member for contacting said sample member.

\* \* \* \* \*